US010268884B2

(12) United States Patent
Jones et al.

(10) Patent No.: US 10,268,884 B2
(45) Date of Patent: Apr. 23, 2019

(54) OPTICAL FINGERPRINT SENSOR UNDER A DISPLAY

(71) Applicant: Synaptics Incorporated, San Jose, CA (US)

(72) Inventors: Eric Jones, Santa Cruz, CA (US); Paul Wickboldt, Walnut Creek, CA (US); Patrick Smith, San Jose, CA (US); Young Seen Lee, Newark, CA (US); Alvin Jee, San Jose, CA (US); Richard Andrew Klenkler, San Jose, CA (US); Bob Lee Mackey, San Jose, CA (US)

(73) Assignee: Synaptics Incorporated, San Jose, CA (US)

( * ) Notice: Subject to any disclaimer, the term of this patent is extended or adjusted under 35 U.S.C. 154(b) by 162 days.

(21) Appl. No.: 15/199,774

(22) Filed: Jun. 30, 2016

(65) Prior Publication Data
US 2017/0220844 A1    Aug. 3, 2017

Related U.S. Application Data

(60) Provisional application No. 62/289,172, filed on Jan. 29, 2016.

(51) Int. Cl.
*G06K 9/00* (2006.01)
*G06F 3/041* (2006.01)
(Continued)

(52) U.S. Cl.
CPC .......... *G06K 9/0053* (2013.01); *A61B 5/0059* (2013.01); *A61B 5/1172* (2013.01);
(Continued)

(58) Field of Classification Search
CPC ............ G06K 9/0053; G06K 9/00013; G06K 9/00026; G06K 9/0004; G06K 9/0008;
(Continued)

(56) References Cited

U.S. PATENT DOCUMENTS 5,726,443 A * 3/1998 Immega ................ G01S 17/026
                                                              250/208.1
6,856,383 B1    2/2005 Vachris et al.
(Continued)

FOREIGN PATENT DOCUMENTS

CN            10273860 A      5/2011
CN           102073860 A  †   5/2011
(Continued)

OTHER PUBLICATIONS

U.S. Appl. No. 62/078,727, filed Nov. 12, 2014.
(Continued)

*Primary Examiner* — Manav Seth
(74) *Attorney, Agent, or Firm* — Leydig, Voit & Mayer, Ltd.

(57) ABSTRACT

An optical sensor system includes: an input surface providing a sensing region for a biometric object; a plurality of display elements, disposed beneath the input surface, configured to emit light to provide a display; an aperture layer, disposed beneath the plurality of display elements; a collimator layer, disposed beneath the aperture layer; and a plurality of light sensing elements, disposed beneath the collimator layer, wherein the plurality of light sensing elements are configured to detect light from the sensing region that has passed through the aperture layer and the collimator layer.

27 Claims, 13 Drawing Sheets

(51) Int. Cl.
| | |
|---|---|
| *G02B 27/30* | (2006.01) |
| *G02B 27/28* | (2006.01) |
| *A61B 5/1172* | (2016.01) |
| *H01L 27/32* | (2006.01) |
| *H04N 5/225* | (2006.01) |
| *A61B 5/00* | (2006.01) |
| *G02B 13/24* | (2006.01) |
| *G06F 3/042* | (2006.01) |
| *A61B 5/1455* | (2006.01) |
| *A61B 5/026* | (2006.01) |

(52) U.S. Cl.
CPC ........... *G02B 13/24* (2013.01); *G02B 27/286* (2013.01); *G02B 27/30* (2013.01); *G06F 3/0412* (2013.01); *G06F 3/0421* (2013.01); *G06K 9/0004* (2013.01); *G06K 9/00013* (2013.01); *G06K 9/00026* (2013.01); *H01L 27/3234* (2013.01); *H04N 5/2253* (2013.01); *H04N 5/2254* (2013.01); *A61B 5/0261* (2013.01); *A61B 5/14552* (2013.01); *G02B 2207/123* (2013.01); *G06F 2203/0338* (2013.01); *G06F 2203/04103* (2013.01); *G06K 9/0008* (2013.01); *G06K 2009/0006* (2013.01); *G06K 2009/00939* (2013.01)

(58) Field of Classification Search
CPC . G06K 2009/0006; G06K 2009/00939; G02B 13/24; G02B 27/286; G02B 27/30; G02B 2207/123; G06F 3/0412; G06F 3/0421; G06F 2203/0338; G06F 2203/04103; H04N 5/2253; H04N 5/2254; A61B 5/0059; A61B 5/1172; A61B 5/0261; A61B 5/14552; H01L 27/3234
See application file for complete search history.

(56) References Cited

U.S. PATENT DOCUMENTS

| | | | |
|---|---|---|---|
| 7,697,053 B2 | 4/2010 | Kurtz et al. | |
| 7,808,540 B2 | 10/2010 | Cok | |
| 8,593,503 B2 | 11/2013 | Bolle | |
| 8,994,690 B2 | 3/2015 | Shi et al. | |
| 9,574,757 B2 * | 2/2017 | Omata | G06F 3/044 |
| 9,754,526 B2 * | 9/2017 | Evans V | H04N 7/144 |
| 9,817,520 B2 * | 11/2017 | Ikeda | G06F 3/042 |
| 9,865,665 B2 * | 1/2018 | Eguchi | G06F 3/044 |
| 2004/0164953 A1 | 8/2004 | Keranen et al. | |
| 2004/0252867 A1 * | 12/2004 | Lan | G06K 9/0004 382/124 |
| 2004/0263670 A1 | 12/2004 | Yamasaki | |
| 2006/0007222 A1 | 1/2006 | Uy | |
| 2009/0141116 A1 | 6/2009 | Kanade et al. | |
| 2010/0034433 A1 | 2/2010 | Thiebot et al. | |
| 2010/0066800 A1 | 3/2010 | Ryf et al. | |
| 2011/0102308 A1 | 5/2011 | Nakamura et al. | |
| 2011/0102569 A1 | 5/2011 | Erhart | |
| 2011/0285680 A1 | 11/2011 | Nakamura | |
| 2012/0113160 A1 | 5/2012 | Kurokawa | |
| 2012/0162490 A1 | 6/2012 | Chung | |
| 2012/0167170 A1 | 6/2012 | Shi et al. | |
| 2013/0135268 A1 | 5/2013 | Kanade et al. | |
| 2013/0135328 A1 | 5/2013 | Rappoport et al. | |
| 2013/0287272 A1 | 10/2013 | Lu et al. | |
| 2013/0287274 A1 | 10/2013 | Shi et al. | |
| 2013/0293459 A1 | 11/2013 | Nakamura et al. | |
| 2014/0016071 A1 | 1/2014 | Yang et al. | |
| 2014/0037257 A1 | 2/2014 | Yang et al. | |
| 2014/0092028 A1 | 4/2014 | Prest et al. | |
| 2014/0092346 A1 | 4/2014 | Yang et al. | |
| 2014/0129843 A1 | 5/2014 | Shi et al. | |
| 2014/0218327 A1 * | 8/2014 | Shi | G06F 3/041 345/174 |
| 2014/0292666 A1 | 10/2014 | Shi et al. | |
| 2015/0036065 A1 | 2/2015 | Yousefpor et al. | |
| 2015/0109214 A1 * | 4/2015 | Shi | G06F 3/044 345/173 |
| 2015/0154436 A1 | 6/2015 | Shi et al. | |
| 2015/0331508 A1 * | 11/2015 | Nho | G06F 3/0421 345/173 |
| 2015/0347813 A1 | 12/2015 | Tsen | |
| 2015/0379323 A1 | 12/2015 | Erhart et al. | |
| 2016/0132712 A1 * | 5/2016 | Yang | G06K 9/0002 348/77 |
| 2016/0224816 A1 | 8/2016 | Smith et al. | |
| 2016/0247010 A1 * | 8/2016 | Huang | G02B 5/20 |
| 2016/0274398 A1 * | 9/2016 | Hirakata | G06F 3/0416 |
| 2016/0328051 A1 * | 11/2016 | Shishido | G06F 3/044 |
| 2017/0124370 A1 | 5/2017 | He et al. | |
| 2017/0156651 A1 † | 6/2017 | Arias | |
| 2017/0220840 A1 * | 8/2017 | Wickboldt | G06K 9/0053 |

FOREIGN PATENT DOCUMENTS

| | | |
|---|---|---|
| EP | 0886958 B1 | 4/2001 |
| WO | WO 2015041459 A1 | 3/2016 |
| WO | WO 2016015009 A1 | 3/2016 |
| WO | WO 2016/154378 A1 | 9/2016 |
| WO | WO 2017/129126 A1 | 8/2017 |

OTHER PUBLICATIONS

U.S. Appl. No. 61/138,107, filed Mar. 25, 2015.
U.S. Appl. No. 62/249,832, filed Nov. 2, 2015.
U.S. Appl. No. 62/289,328, filed Jan. 31, 2016.
U.S. Appl. No. 62/330,833, filed May 2, 2016.
U.S. Appl. No. 62/347,073, filed Jun. 7, 2016.
English translation of CN 102073860 submitted with Third Party Submission under 37 CFR 1.290 in U.S. Appl. No. 15/199,774, filed Oct. 26, 2017.
Claire M. Lochner et al., All-organic optoelectronic sensor for pulse oximetry, Nature Communications, Dec. 10, 2014, Macmillian Publishers Limited.
Lochner, Claire M., et al. "All-organic optoelectronic sensor for pulse oximetry." *Nature communications* 5 Article No. 5745, DOI: 10.1038/ncomms6745, Dec. 10, 2014.
U.S. Appl. No. 15/199,856, filed Jun. 30, 2016.
International Search Report and Written Opinion issued in PCT/US2017/015107 dated Apr. 25, 2017.
Claire M. Lochner et al.,All-organic optoelectronic sensor for pulse oximetry, 12 pages, Published Dec. 10, 2014, published by Nature Communications, Macmillan Publishers Limited.†

* cited by examiner
† cited by third party

US 10,268,884 B2

OPTICAL FINGERPRINT SENSOR UNDER A DISPLAY

CROSS-REFERENCE TO RELATED APPLICATION

This patent application claims the benefit of U.S. Provisional Patent Application No. 62/289,172, filed Jan. 29, 2016, which is incorporated by reference.

BACKGROUND

Input devices, including touch sensor devices (also commonly called touchpads or proximity sensor devices), as well as fingerprint sensor devices, are widely used in a variety of electronic systems.

Touch sensor devices typically include a sensing region, often demarked by a surface, in which the touch sensor device determines the presence, location and/or motion of one or more input objects, typically for purposes allowing a user to provide user input to interact with the electronic system.

Fingerprint sensor devices also typically include a sensing region in which the fingerprint sensor device determines presence, location, motion, and/or features of a fingerprint or partial fingerprint, typically for purposes relating to user authentication or identification of a user.

Touch sensor devices and fingerprint sensor devices may thus be used to provide interfaces for the electronic system. For example, touch sensor devices and fingerprint sensor devices are often used as input devices for larger computing systems (such as opaque touchpads and fingerprint readers integrated in or peripheral to notebook or desktop computers). Touch sensor devices and fingerprint sensors are also often used in smaller computing systems (such as touch screens integrated in mobile devices such as smartphones and tablets).

SUMMARY

In an exemplary embodiment, an optical sensor system includes: an input surface providing a sensing region for a biometric object; a plurality of display elements, disposed beneath the input surface, configured to emit light to provide a display; an aperture layer, disposed beneath the plurality of display elements; a collimator layer, disposed beneath the aperture layer; and a plurality of light sensing elements, disposed beneath the collimator layer, wherein the plurality of light sensing elements are configured to detect light from the sensing region that has passed through the aperture layer and the collimator layer.

In another exemplary embodiment, an optical sensor system includes: an input surface providing a sensing region for a biometric object; a plurality of display elements, disposed beneath the input surface, configured to emit light to provide a display; a pinhole layer, comprising a plurality of pinholes, disposed beneath the plurality of display elements; and an image sensor, disposed beneath the pinhole layer, wherein the image sensor is configured to detect a plurality of sub-images corresponding to the biometric object, each sub-image of the plurality of sub-images being projected onto the image sensor by a respective pinhole of the pinhole layer.

In yet another exemplary embodiment, an optical sensor system includes: an input surface providing a sensing region for a biometric object; a plurality of display elements, disposed beneath the input surface, configured to emit light to provide a display, wherein the plurality of display elements include sub-pixels corresponding to red light and sub-pixels corresponding to green light; an image sensor, disposed beneath the plurality of display elements, configured to detect light from the plurality of display elements that is reflected from the sensing region; and a processor, configured to cause the plurality of display elements to alternately illuminate the biometric object with red light and green light using the plurality of display elements, and to detect, based on detection of red light and green light reflected from the sensing region by the image sensor, a pulse corresponding to the biometric object.

In yet another exemplary embodiment, an optical sensor system includes: an input surface providing a sensing region for a biometric object; a plurality of display elements, disposed beneath the input surface, configured to emit light to provide a display; an aperture layer, disposed beneath the plurality of display elements, configured to diffract light from the plurality of display elements reflected from the sensing region; and an image sensor, disposed beneath the aperture layer, wherein the image sensor is configured to detect the diffraction patterns of the diffracted light.

In yet another exemplary embodiment, a method for producing an optical biometric sensor for a display device includes: forming a display stack, wherein the display stack includes an input surface providing a sensing region for a biometric object and a plurality of display elements configured to emit light to provide a display; forming a biometric object sensor, the biometric object sensor includes a collimator layer and a plurality of light sensing elements; forming an aperture layer; and attaching the biometric object sensor to the display stack.

In yet another exemplary embodiment, a method for using an optical biometric sensor to detect vascular information relating to a biometric object includes: illuminating, by a plurality of display elements of a display device, a biometric object above a cover lens of the display device with green and red light in an alternating manner; and detecting, by a plurality of light sensing elements of the display device, green and red light, respectively, reflected from a sensing region above the cover lens during the illuminating, wherein the reflected light passes through an aperture layer and a collimator layer of the display device before being detected; and detecting, by a processor of the display device, a pulse corresponding to the biometric object based on the detected green and red light.

DETAILED DESCRIPTION

The following detailed description is exemplary in nature and is not intended to limit the disclosure or the application and uses of the disclosure. Furthermore, there is no intention to be bound by any expressed or implied theory presented in the preceding background and brief description of the drawings, or the following detailed description.

Exemplary embodiments of this disclosure provide for light collimation for an optical sensor located under a display. By using an aperture layer together with a collimator layer, various advantages are achieved with respect to achieving a relatively high aspect ratio for an optical sensing system using a cost-effective structure that is relatively easy to manufacture.

Further exemplary embodiments utilizing a pinhole layer, diffraction imaging, and pulse detection with respect to an optical sensor under a display are also contemplated and discussed herein.

Figure 1:
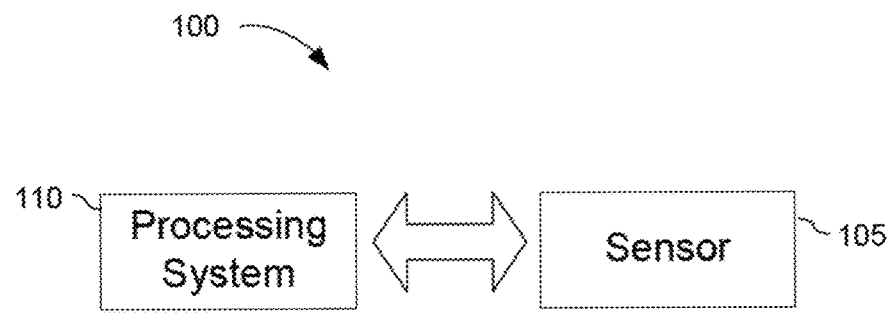
FIG. 1 is a block diagram of an example input device.

FIG. 1 is a block diagram of an example input device 100. The input device 100 may be configured to provide input to an electronic system (not shown). As used in this document, the term "electronic system" (or "electronic device") broadly refers to any system capable of electronically processing information. Some non-limiting examples of electronic systems include personal computers of all sizes and shapes, such as desktop computers, laptop computers, netbook computers, tablets, web browsers, e-book readers, personal digital assistants (PDAs), and wearable computers (such as smart watches and activity tracker devices). Additional examples of electronic systems include composite input devices, such as physical keyboards that include input device 100 and separate joysticks or key switches. Further examples of electronic systems include peripherals such as data input devices (including remote controls and mice), and data output devices (including display screens and printers). Other examples include remote terminals, kiosks, and video game machines (e.g., video game consoles, portable gaming devices, and the like). Other examples include communication devices (including cellular phones, such as smart phones), and media devices (including recorders, editors, and players such as televisions, set-top boxes, music players, digital photo frames, and digital cameras). Additionally, the electronic system could be a host or a slave to the input device.

The input device 100 can be implemented as a physical part of the electronic system, or can be physically separate from the electronic system. As appropriate, the input device 100 may communicate with parts of the electronic system using any one or more of the following: buses, networks, and other wired or wireless interconnections. Examples include I2C, SPI, PS/2, Universal Serial Bus (USB), Bluetooth, RF, and IRDA.

In FIG. 1, a sensor 105 is included with the input device 100. The sensor 105 comprises one or more sensing elements configured to sense input provided by one or more input objects in a sensing region. Examples of input objects include fingers, styli, and hands. Sensing region encompasses any space above, around, in and/or near the sensor 105 in which the input device 100 is able to detect user input (e.g., user input provided by one or more input objects). The sizes, shapes, and locations of particular sensing regions may vary from embodiment to embodiment. In some embodiments, the sensing region extends from a surface of the input device 100 in one or more directions into space until signal-to-noise ratios prevent sufficiently accurate object detection. The distance to which this sensing region extends in a particular direction, in various embodiments, may be on the order of less than a millimeter, millimeters, centimeters, or more, and may vary significantly with the type of sensing technology used and the accuracy desired. Thus, some embodiments sense input that comprises no contact with any surfaces of the input device 100, contact with an input surface (e.g., a touch surface) of the input device 100, contact with an input surface of the input device 100 coupled with some amount of applied force or pressure, and/or a combination thereof. In various embodiments, input surfaces may be provided by surfaces of sensor substrates within which or on which sensor elements are positioned, or by face sheets or other cover layers positioned over sensor elements.

The input device 100 may utilize optical sensing techniques where one or more sensing elements detect light from the sensing region. The detected light may be reflected from the input object, transmitted through the input object, emitted by input object, or some combination thereof. The detected light may be in the visible or invisible spectrum (such as infrared or ultraviolet light). Example optical sensing elements include photodiodes, CMOS image sensor arrays, CCD arrays, photodiodes, and other suitable photosensors sensitive to light in wavelength(s) of interest. Active illumination may be used to provide light to the sensing region, and reflections from the sensing region in the illumination wavelength(s) may be detected to determine input information corresponding to the input object.

One example optical technique utilizes direct illumination of the input object, which may or may not be in contact with an input surface of the sensing region depending on the configuration. One or more light sources and/or light guiding structures are used to direct light to the sensing region. When an input object is present, this light is reflected directly from surfaces of the input object, which reflections can be detected by the optical sensing elements and used to determine input information about the input object.

Another example optical technique utilizes indirect illumination based on internal reflection to detect input objects in contact with an input surface of the sensing region. One or more light sources are used to direct light in a transmitting medium at an angle at which it is internally reflected at the input surface of the sensing region, due to different refractive indices at opposing sides of the interface defined by the input surface. Contact of the input surface by the input object causes the refractive index to change across this boundary, which alters the internal reflection characteristics at the input surface. Higher contrast signals can often be achieved if principles of frustrated total internal reflection (FTIR) are used to detect the input object, where the light is directed to the input surface at an angle of incidence at which it is totally internally reflected, except at locations where the input object is in contact and causes the light to partially transmit across this interface. An example of this is presence of a finger introduced to an input surface defined by a glass to air interface. The higher refractive index of human skin compared to air causes light incident at the input surface at the critical angle of the interface to air to be partially transmitted through the finger, where it would otherwise be totally internally reflected at the glass to air interface. This optical response can be detected by the system and used to determine spatial information. In some embodiments, this can be used to image small scale surface variations of the input object, such as fingerprint patterns, where the internal reflectivity of the incident light differs depending on whether a ridge or valley of the finger is in contact with that portion of the input surface.

In FIG. 1, a processing system 110 is included with the input device 100. The processing system 110 comprises parts of or all of one or more integrated circuits (ICs) and/or other circuitry components. The processing system 110 is coupled to the sensor 105, and is configured to detect input in the sensing region using sensing hardware of the sensor 105.

The processing system 110 may include driver circuitry configured to drive sensing signals with sensing hardware of the input device 100 and/or receiver circuitry configured to receive resulting signals with the sensing hardware. For example, a processing system for an optical sensor device may comprise driver circuitry configured to drive illumination signals to one or more LEDs or other light sources, and/or receiver circuitry configured to receive signals with optical receiving elements.

The processing system 110 may include electronically-readable instructions, such as firmware code, software code, and/or the like. The processing system 110 can be implemented as a physical part of the sensor 105, or can be physically separate from the sensor 105. Also, constituent components of the processing system 110 may be located together, or may be located physically separate from each other. For example, the input device 100 may be a peripheral coupled to a computing device, and the processing system 110 may comprise software configured to run on a central processing unit of the computing device and one or more ICs (e.g., with associated firmware) separate from the central processing unit. As another example, the input device 100 may be physically integrated in a mobile device, and the processing system 110 may comprise circuits and firmware that are part of a main processor of the mobile device. The processing system 110 may be dedicated to implementing the input device 100, or may perform other functions, such as operating display screens, driving haptic actuators, etc.

The processing system 110 may operate the sensing element(s) of the input device 100 to produce electrical signals indicative of input (or lack of input) in a sensing region. The processing system 110 may perform any appropriate amount of processing on the electrical signals in producing the information provided to the electronic system. For example, the processing system 110 may digitize analog electrical signals obtained from the sensor electrodes. As another example, the processing system 110 may perform filtering or other signal conditioning. As yet another example, the processing system 110 may subtract or otherwise account for a baseline, such that the information reflects a difference between the electrical signals and the baseline. As yet further examples, the processing system 110 may determine positional information, recognize inputs as commands, recognize handwriting, match biometric samples, and the like.

The sensing region of the input device 100 may overlap part or all of an active area of a display device, for example, if the sensor 105 provides a touch screen interface. The display device may be any suitable type of dynamic display capable of displaying a visual interface to a user, including an inorganic light emitting diode (LED) display, organic LED (OLED) display, cathode ray tube (CRT), liquid crystal display (LCD), plasma display, electroluminescence (EL) display, or other display technology. The display may be flexible or rigid, and may be flat, curved, or have other geometries. The display may include a glass or plastic substrate for TFT circuitry, which may be used to address display pixels for providing visual information and/or providing other functionality. The display device may include a cover lens (sometimes referred to as a "cover glass") disposed above display circuitry and above inner layers of the display module, and the cover lens may also provide an input surface for the input device 100. Examples of cover lens materials include optically clear amorphous solids, such as chemically hardened glass, and optically clear crystalline structures, such as sapphire. The input device 100 and the display device may share physical elements. For example, some of the same electrical components may be utilized for both displaying visual information and for input sensing with the input device 100, such as using one or more display electrodes for both display updating and input sensing. As another example, the display screen may be operated in part or in total by the processing system 110 in communication with the input device.

Figure 2A:
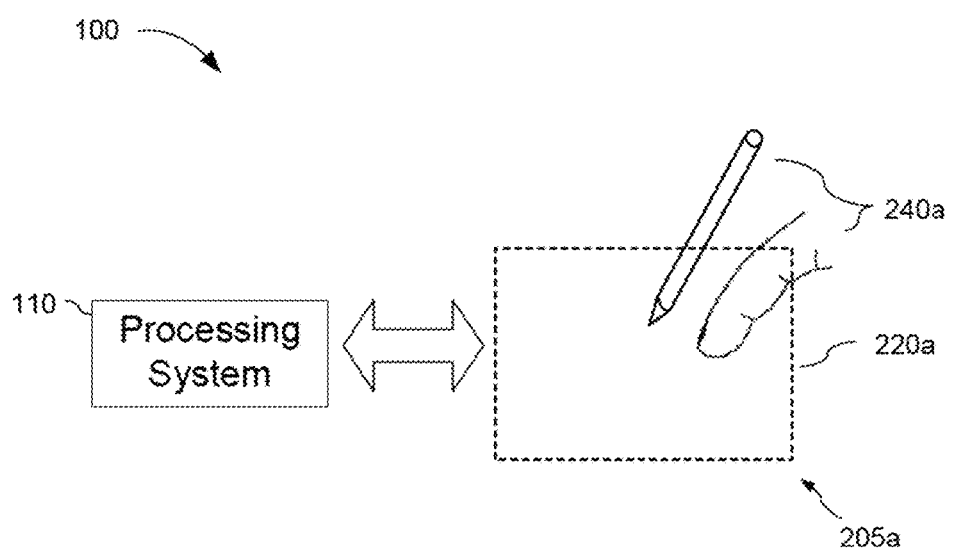
FIG. 2A is a block diagram of another example input device.
Figure 2B:
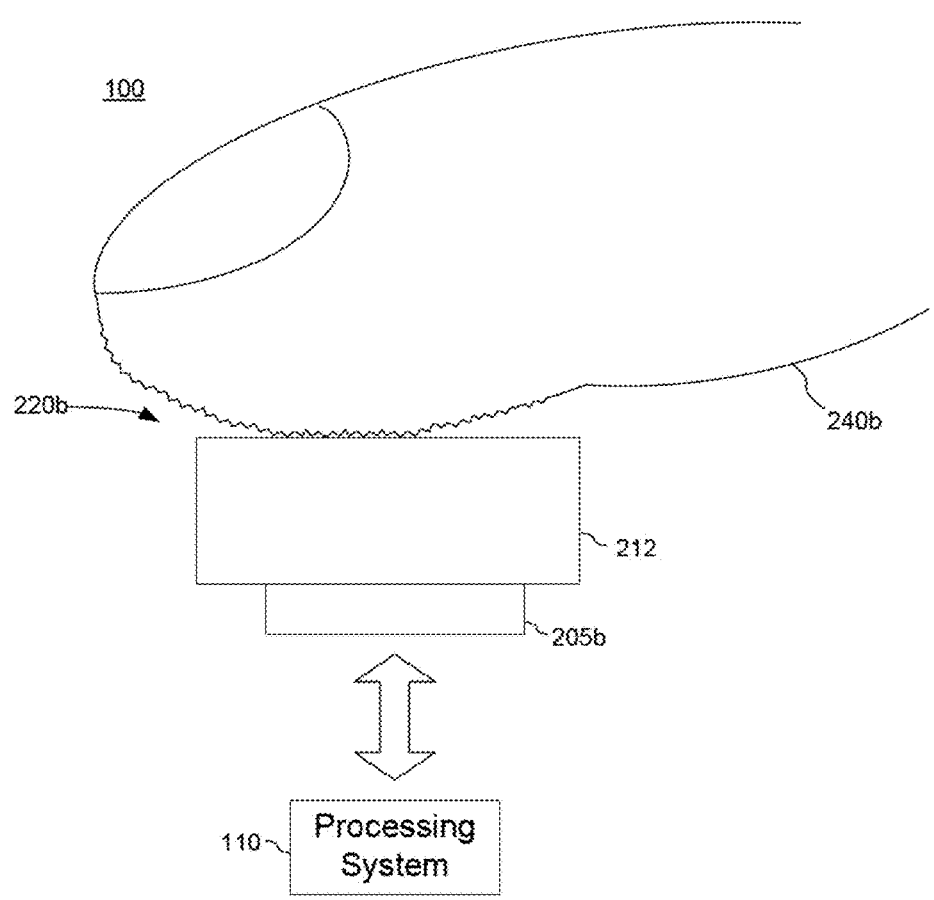
FIG. 2B is a block diagram of another example input device.

FIGS. 2A-2B depict further example input devices 100. In FIG. 2A, the input device 100 is shown as including a touch sensor 205a. The touch sensor 205a is configured to detect position information of an input object 240a within the sensing region 220a. The input object 240a may include a finger or a stylus, as shown in FIG. 2A. The sensing region 220a may include an input surface having a larger area than the input object. The touch sensor 205a may include an array of sensing elements with a resolution configured to detect a location of a touch to the input surface.

In FIG. 2B, the input device 100 is shown as including a fingerprint sensor 205b. The fingerprint sensor 205b is configured to capture a fingerprint from a finger 240b. The sensor 205b is disposed underneath a cover layer 212 that provides an input surface for the fingerprint to be placed on or swiped over the sensor 205b. The sensing region 220b may include an input surface with an area larger than, smaller than, or similar in size to a full fingerprint. The fingerprint sensor 205b has an array of sensing elements with a resolution configured to detect surface variations of the finger 240b, and the fingerprint sensor 205b has a higher resolution than the touch sensor 205a of FIG. 2A.

Figure 3A:
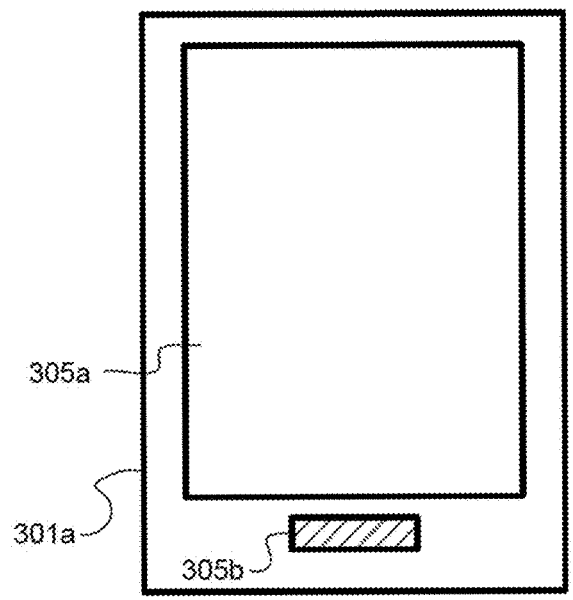
FIGS. 3A-3B are block diagrams illustrating example electronic devices having both a touch screen interface and a fingerprint sensing interface.
Figure 3B:
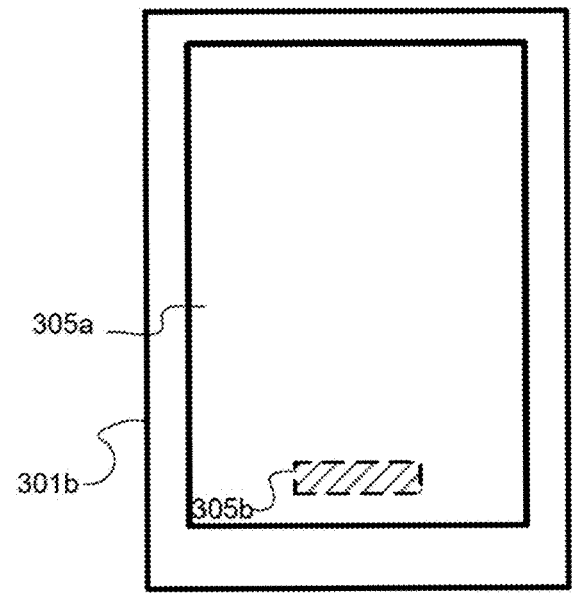

FIGS. 3A-3B are block diagrams illustrating example electronic devices 301a and 301b having both a display and a fingerprint sensing interface. In FIG. 3A, the electronic device (e.g., a mobile device, such as a smartphone or tablet) 301a has a fingerprint sensor 305b that is separate from the active display area 305a. In FIG. 3B, the electronic device 301b has a fingerprint sensor 305b that is integrated within the active display area 305a, such that the interface for the fingerprint sensor overlaps with the interface for the touch sensor. In FIGS. 3A-3B, a touch sensor interface may also overlap with the active area of the display, such that in FIG. 3B the active display area includes both a fingerprint sensing and touch sensing interface.

The configuration in FIG. 3B is desirable as it allows removal of a home button located on the front cover glass, providing opportunities for both improved cosmetic design and increasing display area. To achieve the configuration in FIG. 3B, in some embodiments, an optical fingerprint sensor (OFPS) may be placed under a semi-transparent display, with an aperture layer in and/or below the semi-transparent display and a collimator for providing relatively improved optical resolution.

An exemplary application for embodiments of the disclosure is a fingerprint sensor for a mobile device. In conventional fingerprint sensors for mobile devices, the fingerprint sensor is often located under or proximate to a button of the mobile device rather than in a display portion of the device. While enhanced fingerprint imaging through thicker material stacks (e.g., coverglass, touch sensor, adhesives and display) may be made possible by collimating light directly above an optical fingerprint sensor (OFPS) to provide a given aspect ratio defined by the dimensions of a collimator (i.e., column height:column opening), manufacturing collimators with high aspect ratios (such as 15:1 or greater) can be costly or impracticable, as collimator costs become increasingly higher and manufacturing becomes increasingly difficult and/or impossible as the aspect ratio increases.

Exemplary embodiments of the disclosure, however, allow for an optical fingerprint sensor to be provided under a semi-transparent display by introducing a separate aperture layer to be used in combination with a collimator layer. This reduces the collimator cost for a given optical resolution and allows sensing underneath a display (at a location where the optical sensor avoids interfering with the appearance of displayed graphics). Using the combined aperture and collimator approach may also avoid sensor pixel cross-talk.

Exemplary embodiments of the disclosure thus allow manufacture of mobile devices with relatively larger display areas and/or without the presence of a "home" button while maintaining the availability of biometric security features. For example, placing an optical fingerprint sensor under a semi-transparent display enables larger display and monolithic coverglass without a fingerprint sensor button, and may also avoid the need to cosmetically hide the optical fingerprint sensor or match any decorative coatings because the sensor is hidden under the display.

This may be achieved, for example in one exemplary embodiment, by utilizing an aperture layer in and/or below the display together with a collimator to provide for reduced thickness and cost (relative to collimators in conventional optical fingerprint sensors) and to enable a high effective aspect ratio.

Figure 4:
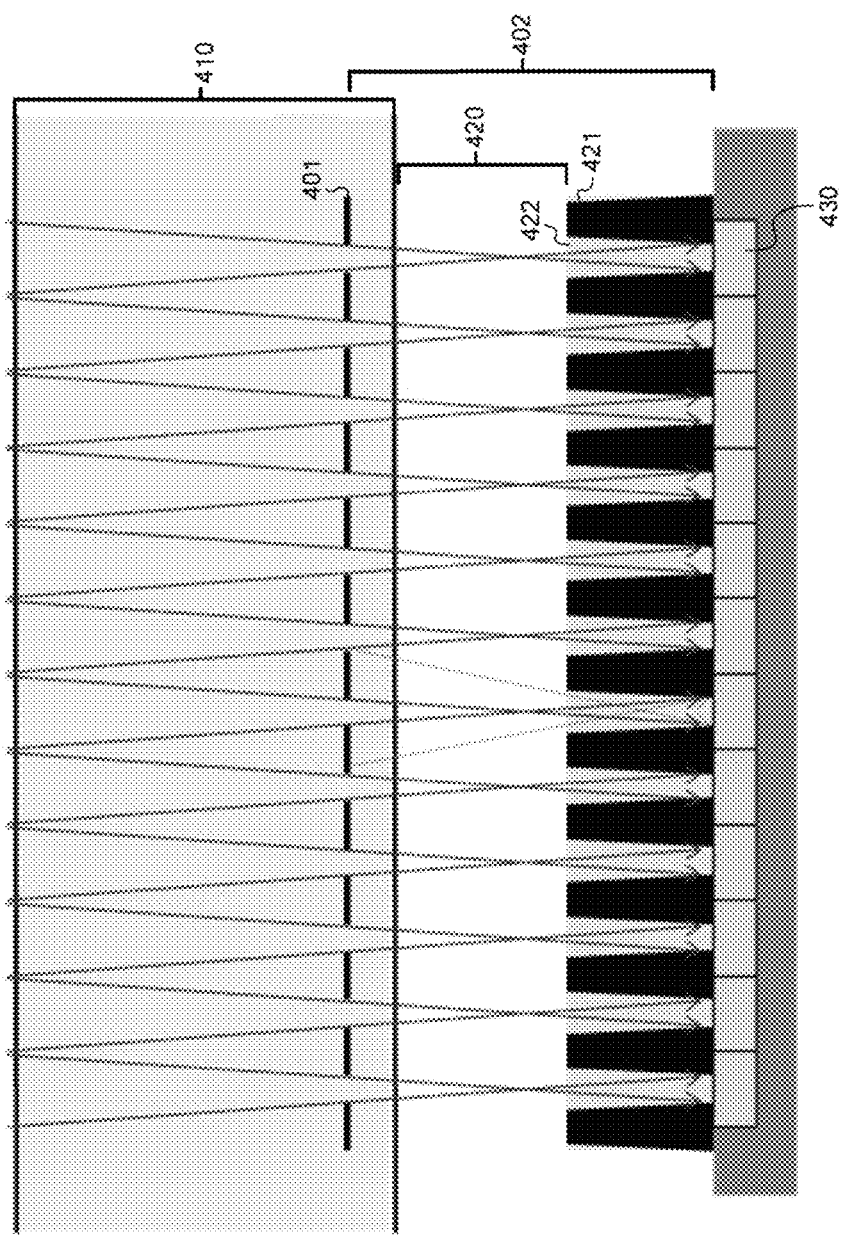
FIG. 4 is a block diagram of an example optical fingerprint sensor with an aperture layer (in a display stack) and a collimating filter layer.

FIG. 4 is a block diagram of an example optical fingerprint sensor with an aperture layer 401 in a display stack and a collimating filter layer 402. In this exemplary embodiment, the aperture layer 401 is disposed in a display (or "display stack") 410 of a device (individual components and layers of the display 410 are not illustrated for simplicity). An input surface providing a sensing region for a biometric object (e.g., a fingerprint) is provided above the display 410. The collimating filter layer (or "collimator layer") 402 is disposed beneath the display 410, and the collimating filter layer 402 may include a gap or a transparent layer 420 and a plurality of light-blocking structures 421. The collimating areas 422 formed between the light-blocking structures may be similar to the array of light collimating apertures or holes as described in U.S. patent application Ser. No. 14/871,810, filed Sep. 30, 2015, to SMITH et al., entitled "OPTICAL SENSOR USING COLLIMATOR," the entire contents of which are hereby incorporated by reference herein. Light sensing elements 430 corresponding to collimating areas 422 are further disposed below the plurality of light-blocking structures 421.

For a given optical resolution, using a combined aperture layer and collimator (i.e., the combination of aperture layer 401 and collimating filter layer 402) reduces the thickness needed for light-blocking structures 421 relative to an optical sensor having a collimating filter layer without an aperture layer (in which case the thickness of the light-blocking structures would need to cover the full distance between the aperture layer 401 and the light sensing elements 430 depicted in FIG. 4). The reduction in collimator thickness can also reduce collimator cost. Due to cost and constraints in manufacturing, an optical sensor structure having an aperture layer in combination with a collimator layer enables higher effective aspect ratios relative to an optical sensor structure relying only on a collimator layer.

The aperture layer 401 includes an array of openings or apertures. The openings of the aperture layer 401 may be aligned to the openings in the collimator filter layer 402 corresponding to the collimating areas 422. In the example shown in FIG. 4, the apertures may be located in or near a TFT layer of display 410 to effectively form entrance apertures for the combined aperture plus collimator layer structure.

In the example shown in FIG. 4, the aperture layer 401 is positioned within the display 410. Semi-transparent displays may make use of lithography for patterning display layer(s). Accordingly, a step of patterning the aperture layer 401 may be included in a process of manufacturing a display stack corresponding to display 410. This can be achieved, for example, by features internal to the outer display stack, external on the outer stack, or a combination thereof. Dimensional details of the aperture layer 401 would depend on design constraints and target effective aspect ratio. Further, alignment features may be used to align the aperture layer 401 in the display stack to the collimating areas 422 (and corresponding light sensing elements 430) under the display 410.

Figure 5:
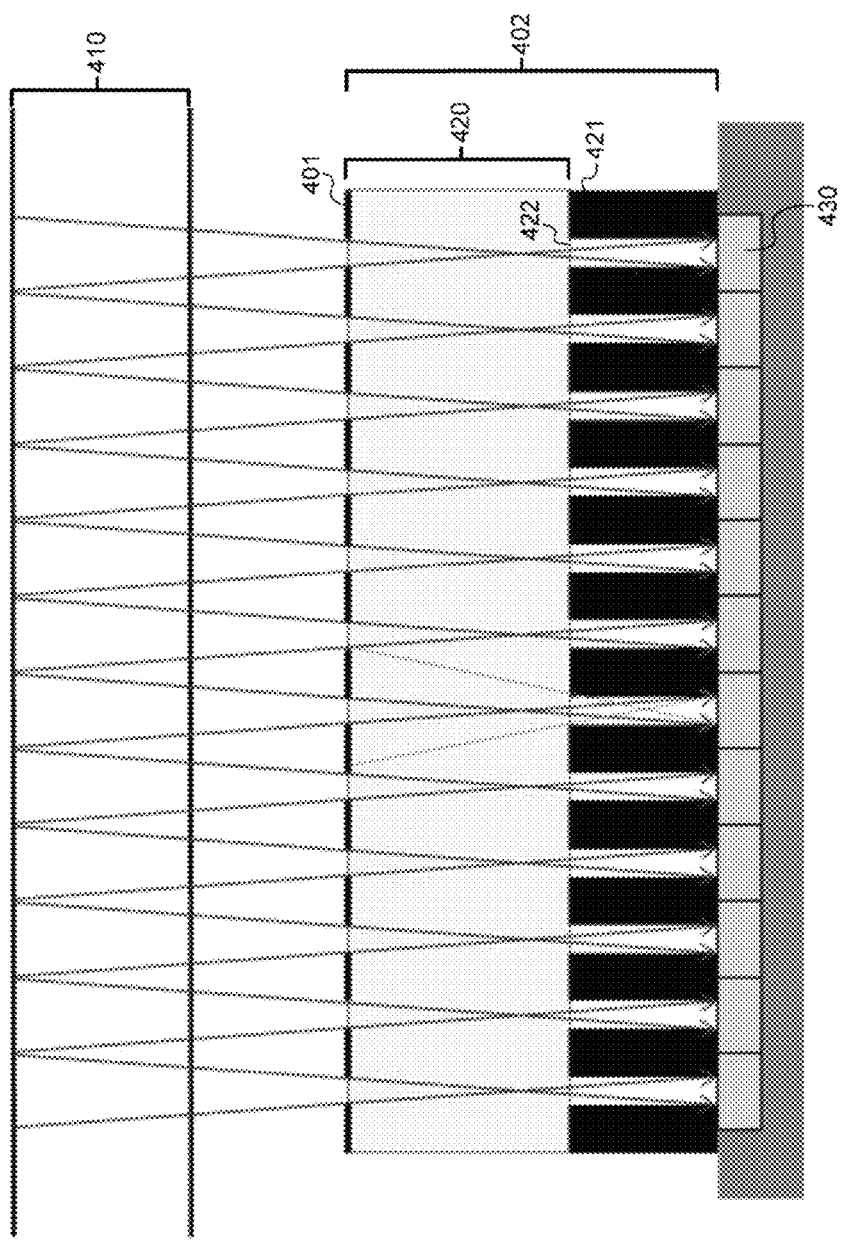
FIG. 5 is a block diagram of an example optical fingerprint sensor with an aperture layer (below a display stack) and a collimating filter layer.

Instead of patterning the apertures in the display stack, the aperture layer may be positioned below the semi-transparent display. An example of this is shown in FIG. 5, which is a block diagram of an example optical fingerprint sensor with an aperture layer 401 (below a display stack 410) and a collimating filter layer 402. The patterned apertures of the aperture layer 401 and the collimating filter layer 402 are separate from the display 410, and may, for example, be part of a standalone optical fingerprint sensor package that is usable in display applications as well as non-display applications. In the case where this standalone optical fingerprint sensor package is used in a display application, alignment features in the display may be used to align apertures in the display to the apertures in the aperture layer of the optical fingerprint sensor package to prevent light-blocking elements of the display from interfering with the optical sensor.

In an exemplary embodiment, the plurality of light-blocking structures 421 with collimating areas 422 are formed using etched silicon having a thickness of up to 100 μm (which provides for relative ease of manufacture), and the combination of the aperture layer 401 with the collimating filter layer 402 provides an aspect ratio of 15:1 or greater (e.g., including 20:1 or 30:1). Further, as can be seen based on the shape of light-blocking structures 421, cross-talk between pixels of the optical sensor (i.e., corresponding to light sensing elements 430) is prevented. The size D of primary apertures in the aperture layer 401 (whether in a TFT layer of a display or a standalone aperture layer) may be chosen to be sufficiently large that the Fraunhofer Distance R ($R\sim2*D^2/\lambda$) is close to the distance from the aperture layer 401 to the top of the light-blocking structures 421. This allows the primary apertures to be made as small as possible, increasing the optical resolution by increasing the aspect ratio, without incurring the loss of resolution associated with diffraction at the primary apertures.

Figure 6:
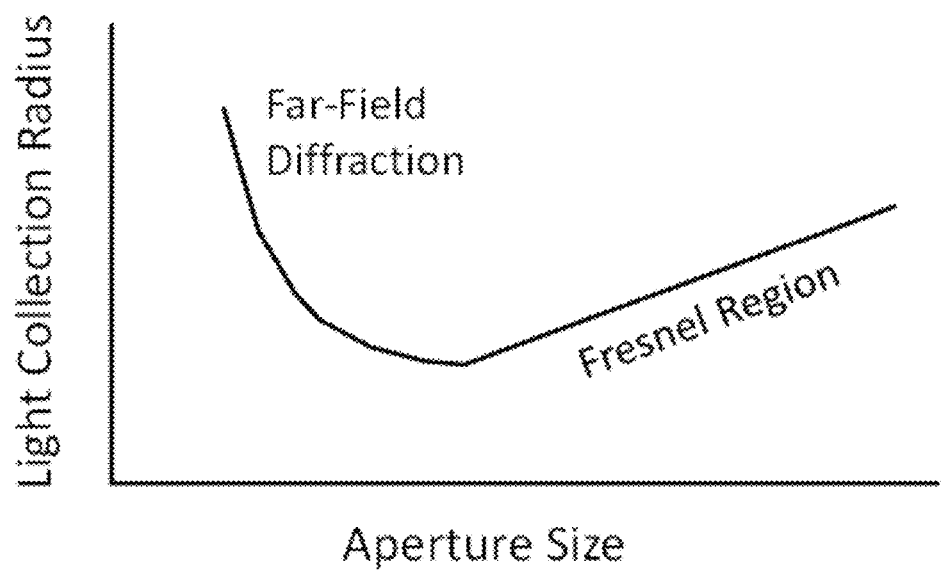
FIG. 6 is an example chart illustrating a trend of the size of the region at the top of collimating areas formed by light-blocking structures that collects a large fraction of the light passing through an aperture.

FIG. 6 is an example chart illustrating a trend of the size of the region at the top of the collimating areas 422 formed by the light-blocking structures 421 that collects a large fraction of the light passing through an aperture of the aperture layer 401 (which may be in a TFT plane in an exemplary embodiment). The transition point between the Fresnel region and Far-Field Diffraction region corresponds to the aperture size at which the Fraunhofer distance is equal to the distance from the aperture to the top of the collimating areas 422 formed by the light-blocking structures 421. As can be seen in FIG. 6, the aperture size can be chosen to produce a minimum size light spot at the top of the collimating areas 422.

The examples depicted above in FIGS. 4 and 5 may be particularly suitable in different situations. For example, providing the aperture layer as part of a self-contained optical fingerprint sensor package as shown in FIG. 5 may be advantageous in that the self-contained optical fingerprint sensor package may be used in under-display and non-under-display applications. Further, it will be appreciated that conventional display stacks, as produced by display manufacturers, may contain a large number of holes through which light may be transmitted, allowing the optical fingerprint sensor package as shown in FIG. 5 to readily be used in combination with such display stacks. In other examples, by determining where holes in a display stack are located, the structure of FIG. 4 may be achieved without needing a specifically-configured aperture layer to be provided (e.g., collimating areas of an optical fingerprint sensor package may be aligned to pre-existing holes in a display stack to achieve the structure of FIG. 4). In other examples, it may be relatively efficient to have display manufacturers specifically configure the display stack to provide apertures such that a separate aperture layer is not needed (e.g., a layer of the display stack is used as the aperture layer as shown in FIG. 4, with the apertures being laid out in a desired configuration and the dimensions of those apertures designed to provide a desired amount of light transmission).

Figure 7:
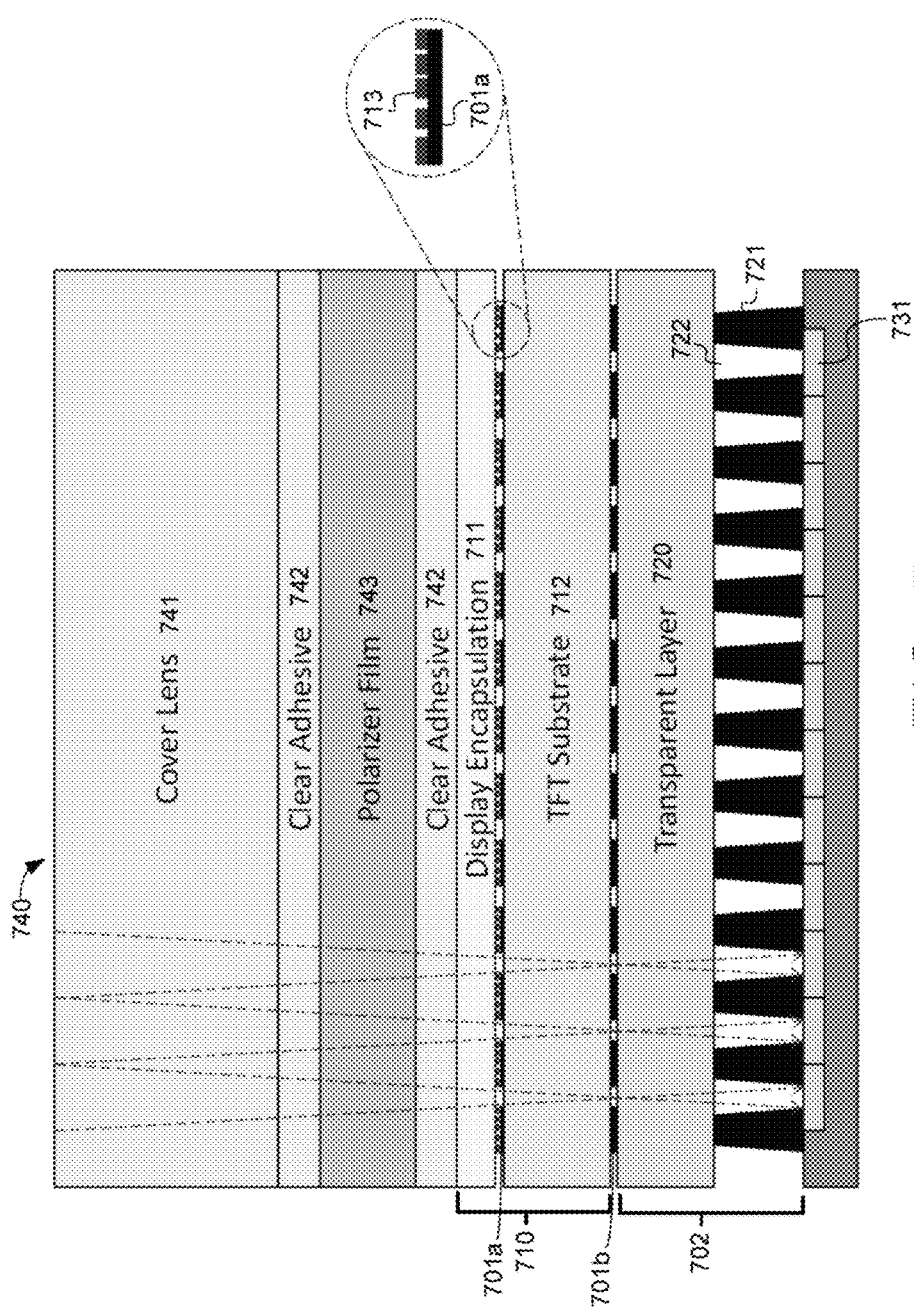
FIG. 7 is a schematic diagram of an example optical fingerprint sensor illustrating details of a display stack and possible configurations of aperture layer(s) with a collimating filter layer.

FIG. 7 is a schematic diagram of an example optical fingerprint sensor illustrating details of a display stack 710 and possible configurations of aperture layer(s) 701a, 701b with a collimating filter layer 702. The display stack 410 may correspond, for example, to a semi-transparent emissive display, and includes a TFT substrate 712, TFT/OLED elements 713, a display encapsulation 711, and an optional light-blocking film with apertures forming an aperture layer 701a. It will be appreciated that the light-blocking film forming the aperture layer 701a may be used to block light from passing through the aperture layer 701a except where the apertures of the aperture layer 701a are provided (e.g., aperture layer 701a blocks light from passing through spaces between features in the TFT/OLED elements of the display stack 710 as depicted on the right side of FIG. 7).

The display stack 710 of the device depicted in FIG. 7 further includes a cover lens 741, above which an input surface 740 provides a sensing region for a biometric input. The cover lens 741 is attached to a polarizer film 743 via clear adhesive 742, and the polarizer film 743 is attached to the display encapsulation 711 via additional clear adhesive 742. An optical fingerprint sensor package is further provided below the display stack 710, which includes collimating filter layer 702 and light sensing elements 731. The collimating filter layer 702 further includes a plurality of light-blocking structures 721, with collimating areas 722 formed between light-blocking structures 721, and a transparent layer 720 (or gap). In an exemplary implementation, the spaces between the light-blocking structures 721, which may be etched silicon collimating structures, may be filed with the same material that is used for the transparent layer 720 to provide for relatively simple manufacturing. In an alternative exemplary implementation, the transparent layer 720 and the collimating areas 722 may instead be left as being filled with air (or be filled with a transparent material with a low index of refraction), providing improved stray light rejection properties for the aperture and collimator system.

Because features in the TFT layer of the display stack 710 may be opaque (for example, metal and silicon features), gaps in these features may act as apertures that transmit light down to the optical fingerprint sensor package. Accordingly, in one exemplary embodiment, neither aperture layer 701a nor aperture layer 701b is used. Instead, an aperture layer may be provided in the display stack 710 based on TFT/OLED elements 713, where spaces/holes between the TFT/OLED elements effectively forms an entrance aperture for the combined aperture and collimator system. Thus, the layout of these TFT/OLED features 713 in the TFT layer of the display stack 710 may be arranged to form primary apertures that are as large as possible, which permits as much light as possible to be transmitted down to the optical fingerprint sensor package and avoids diffraction effects that may be caused by having relatively small apertures (diffraction effects may reduce optical imaging resolution and light collection).

In another exemplary embodiment, aperture layer 701a is used but aperture layer 701b is not used. Aperture layer 701a is a light blocking aperture film that may be added in the TFT layers to define apertures instead of or in conjunction with openings in the TFT patterning formed by TFT/OLED features 713 used for the pixel circuitry of the display stack 710. For example, when gaps in the TFT/OLED features 713 in the TFT layer form small apertures (that are adjacent to or near primary apertures) that could diffract light at wider angles, the optical resolution of the system may be degraded by such diffraction. Accordingly, including the aperture layer 701a as a light blocking aperture film in the TFT layer that blocks these gaps may help to improve the optical sensor's optical resolution.

In yet another exemplary embodiment, aperture layer 701b is used but aperture layer 701a is not used. In this exemplary embodiment, aperture layer 701b provides the primary entrance apertures for the combined aperture and collimator system. Aperture layer 701b may formed on the bottom surface of the TFT substrate 712 (e.g., by coating a patterned opaque layer on the bottom surface of the substrate), or formed separately and attached (e.g., provided as a top layer of a separate discrete sensor module that is attached to the bottom of the substrate, or provided on a separate substrate or film that is attached to a bottom of the TFT substrate 712, under which a separate sensor module is attached).

In yet another exemplary embodiment, both aperture layers 701a and 701b are used. In this exemplary embodiment, aperture layer 701a provides the primary entrance apertures and aperture layer 701b provides apertures which serve to reduce cross-talk between pixels, such that stray light from other pixels does not reach a collimating area 722 corresponding to a particular pixel (e.g., a pixel corresponding to a light-sensing element 731).

In yet another exemplary embodiment, aperture layer 701a is not used, while the primary entrance apertures for the combined aperture and collimator system may be provided in the display stack 710 based on TFT/OLED elements 713, and aperture layer 701b provides apertures which serve to reduce cross-talk between pixels, such that stray light from other pixels does not reach a collimating area 722 corresponding to a particular pixel (e.g., a pixel corresponding to a light-sensing element 731).

In each of these embodiments, the collimating areas 722 are aligned to the light-sensing elements 731, and are also aligned to the primary entrance apertures of the combined aperture and collimator system (whether the primary entrance apertures are formed by gaps between TFT/OLED elements 713, aperture layer 701a, or aperture layer 701b). Further, when aperture layer 701b is used as a secondary aperture layer below the primary entrance apertures to restrict cross-talk, the apertures of aperture layer 701b are also aligned to the primary entrance apertures and to the collimating areas 722 and light-sensing elements 731.

In the example depicted in FIG. 7, source light for illuminating a sensing region on or above the input surface may come from display elements of the display (e.g., light-emitting diodes (LEDs) that are also used to provide the display). In other exemplary embodiments, an auxiliary light source (e,g., one or more discrete LEDs or OLEDs) may be used instead of or in addition to the display as a light source for illuminating the finger. The auxiliary light source may, for example, directly illuminate the fingerprint or may provide light that is directed into the cover glass to utilize the cover glass as a light guide for total internal reflection (TIR) mode illumination. In further exemplary embodiments, environmental or ambient light may be used to illuminate the finger (e.g., sunlight may pass through the finger and be refracted by the fingerprint features), in which case no active illumination of the fingerprint or sensing region is needed. In various implementations, light from the sensing region that is detected by the sensor may be reflected, refracted, or scattered by the biometric object to affect the resulting image captured by the sensor.

The light-blocking structures in FIGS. 4, 5 and 7 may be formed such that the walls defining the respective collimating areas are vertical (as depicted, for example, in FIG. 5) or slanted (or "tapered") (as depicted, for example, in FIGS. 4 and 7). In practice, it may sometimes be advantageous to utilize light-blocking structures having slanted or tapered sidewalls for ease of manufacture and to allow for more tolerance with respect to alignment. The light blocking structures may be formed of etched silicon or a variety of other suitable materials, including plastics such as polycarbonate, PET, polyimide, carbon black, inorganic insulating or metallic materials, or SU-8. The collimating areas 722 may be filled with air or a transparent material. Also, the light blocking structures 721 may be made of one layer, such as silicon with high aspect ratio holes drilled through, or several stacked layers with openings aligned with each other to collectively form a higher aspect ratio light collimating area 722.

It will be appreciated that different embodiments may utilize different apertures shapes for the apertures of the aperture layer. For example, in one exemplary embodiment, the primary entrance apertures may be circular. In another exemplary embodiment, the primary entrance apertures may be non-circular (e.g., rectangular or square-shaped apertures).

Figure 8B:
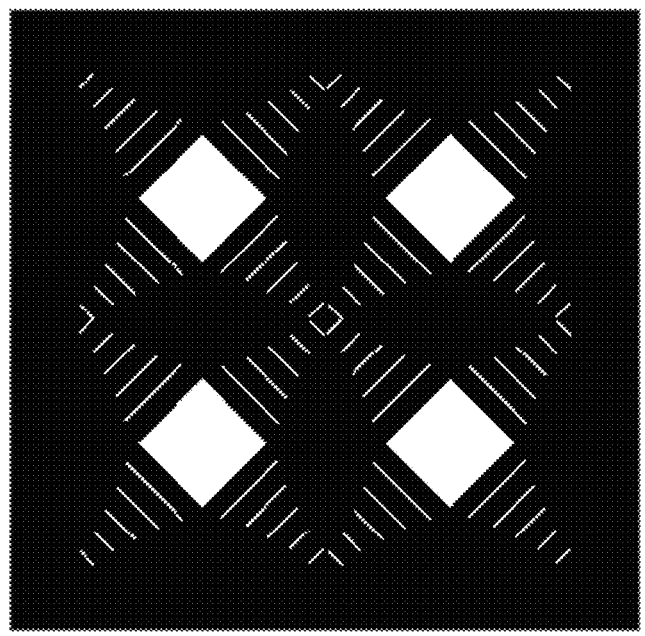
FIG. 8B is an example layout of primary entrance apertures shaped as squares where nearest adjacent apertures are oriented such that the sides of the nearest adjacent apertures do not face each other.
Figure 8A:
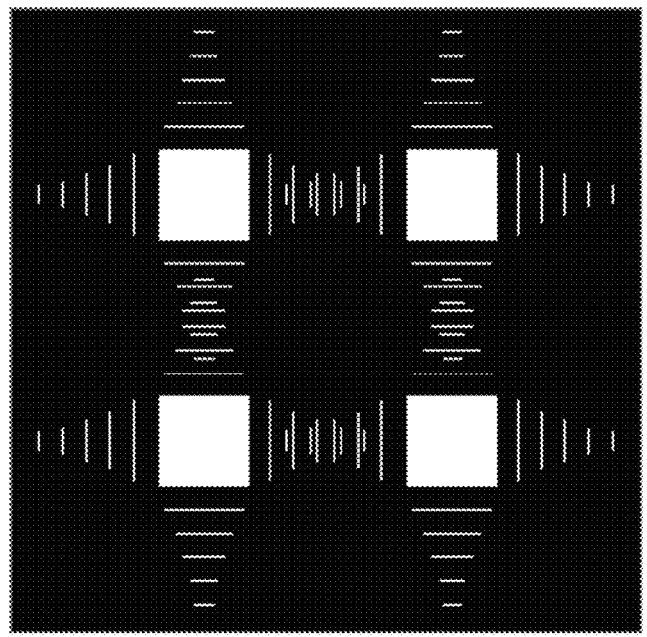
FIG. 8A is an example layout of primary entrance apertures shaped as squares where nearest adjacent apertures are oriented such that the sides of the nearest adjacent apertures face each other.

In embodiments where gaps between elements in the TFT layer of a display stack provide the primary entrance apertures so as to form an aperture layer, the apertures may be rectangular or square due to the pattern in which such elements in the TFT layer are distributed (e.g., due to crisscrossed wiring elements). Other non-circular shapes are possible in other exemplary embodiments. Additionally, because the gaps may be relatively small (e.g., 2-5 µm), these apertures may cause diffraction to occur. The diffraction pattern caused by a square aperture follows the edges of the square, as depicted, for example, in FIGS. 8A and 8B. FIG. 8A is an example layout of non-circular apertures (shaped as squares) where nearest adjacent apertures are oriented such that the sides of the nearest adjacent apertures face each other, including illustrations of diffraction maxima associated with each aperture. FIG. 8B is an example layout of non-circular apertures (shaped as squares) where nearest adjacent apertures are oriented such that the sides of the nearest adjacent apertures do not face each other, including illustrations of diffraction maxima associated with each aperture.

As can be seen from FIGS. 8A and 8B, when nearest adjacent square apertures are arranged such that the sides of the nearest adjacent apertures face each other (see FIG. 8A), the potential for diffraction patterns from one aperture to reach other apertures is greater than the situation where nearest adjacent square apertures are arranged such that the sides of the nearest adjacent apertures do not face each other (see FIG. 8B). In this example using a regular rectangular array, the sides of the apertures are arranged so that they are not parallel to the rows or columns of the array, although it is possible to use other non-rectangular arrays. Thus, when the edges of the apertures are at an angle such that they are not parallel to an aperture array grid (as shown in FIG. 8B), the tendency for light in higher order diffraction maxima to reach other apertures is reduced. Thus, the arrangement shown in FIG. 8B, where the edges of each rectangular or square aperture is rotated relative to its nearest adjacent neighbors (i.e., where the edges face away from the nearest adjacent neighbors), is advantageous relative to the arrangement shown in FIG. 8A with respect to reducing cross-talk and mitigating interaction between nearby apertures.

Figure 9:
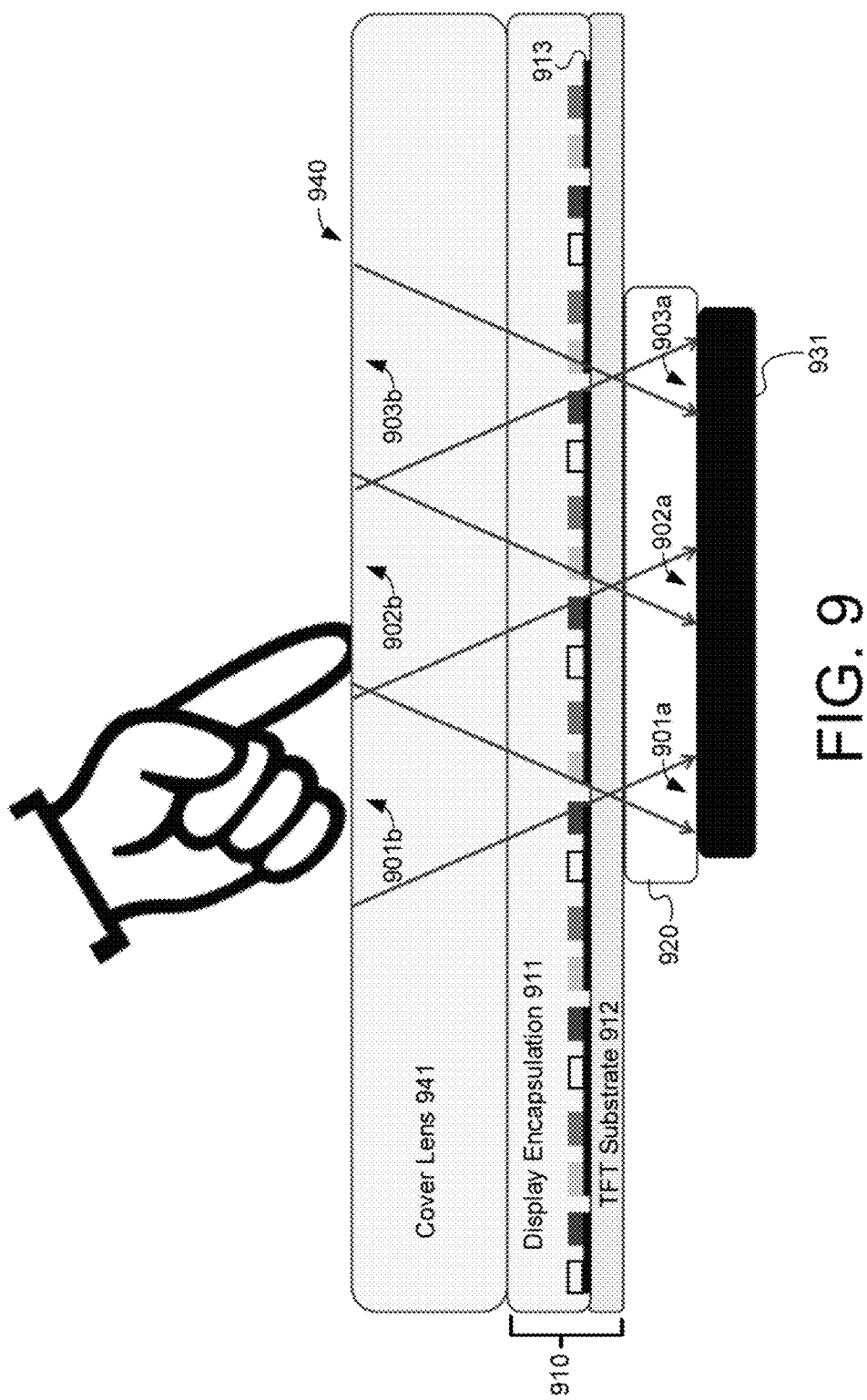
FIG. 9 is a block diagram of an example optical fingerprint sensor with a pinhole layer in a display stack.

In another exemplary embodiment, an optical sensor under a display utilizes a pinhole layer to facilitate imaging of a biometric object through a display. FIG. 9 is a block diagram of an example optical fingerprint sensor device with a pinhole layer 913 in a display stack 910. An array of pinholes are formed in the pinhole layer 913, and each pinhole is configured to project a sub-image (e.g., sub-images 901a, 902a, 903a) corresponding to a respective portion of an input surface 940 of the device (e.g., regions 901b, 902b, 903b at input surface 940) onto a detector array or image sensor 931 below, such as a CMOS image sensor (CIS). It will be appreciated that although FIG. 9 depicts a cross-section, the sub-images 901a, 902a, 903a and their corresponding regions 901b, 902b, 903b at the input surface 940 may be two-dimensional (such as being a circular or square shape). The input surface 940 provides a sensing region at the top of or above a cover lens 941, which is attached to display stack 910. The display stack 910 includes, for example, a TFT substrate 912, display encapsulation 911 encapsulating a plurality of TFT/OLED features, and a pinhole layer 913.

Pinhole layer 913 may be formed in a manner similar to an in-display aperture layer as discussed above with respect to FIGS. 4 and 7. In FIG. 9, pinhole layer 913 is positioned above a transparent TFT substrate (or "display backplane substrate") 912. If the display stack has metal layers or other opaque features, as is common with many OLED displays that use metal features to address individual pixels and/or as bottom electrodes for the OLEDs, pinhole layer 913 may be formed adjacent to or close to these opaque features to avoid intensity reduction or distortion of the light signal in the optical path from the biometric object through the pinholes down to the detector array or image sensor 931. The individual pinholes of pinhole layer 913 may be positioned in areas free of opaque or light blocking features in the display stack. In various exemplary embodiments, the individual pinholes may be positioned in an regular array, or may be positioned in an irregular array or other irregular pattern such that minimal or no changes are required with respect to the pattern of opaque operational features of the display stack 910.

Appropriate image processing by a processing system (not depicted in FIG. 9) may be used to further combine sub-images (e.g., sub-images 901a, 902a, 903a) for fingerprint matching applications. For example, the individual sub-images may each be inverted and stitched together into a larger image for fingerprint verification or enrollment. Known spatial relationships among the individual pinholes, the object plane, and the detector plane, and/or correlations between sub-images in overlapping regions may be used to stitch together the individual sub-images into a larger composite image. Alternatively, the individual sub-images may be mosaicked together in some other fashion, such as one that keeps the individual sub-images separate but preserves transformations that define spatial relationships therebetween.

The individual sub-images may be captured simultaneously or during different time periods. If captured simultaneously, they may be de-convolved as appropriate in cases where the projected sub-images overlap on the detector array or image sensor. To simplify image processing and avoid such deconvolution, a sequence may be used that illuminates different portions of the finger at different times, using the display sub-pixels or other light emitters in the display stack to illuminate the input surface at the top of the cover glass. At each stage in the sequence, only the sub-images captured from below the pinholes corresponding to the currently illuminated region of the fingerprint may be kept, and the sequence may be designed such that portions of the fingerprint corresponding to neighboring sub-images that would otherwise overlap onto the same sets of detector pixels are not illuminated at the same time during the sequence.

In an exemplary implementation, the distribution of pinholes may be such that each pinhole is approximately 800 μm away from an adjacent pinhole.

It will be appreciated that there may be some degree of de-magnification of the sub-images (regions 901b, 902b, 903b are larger than sub-images 901a, 902a, 903a), and it may be advantageous to use a relatively high resolution image sensor 931 for the optical sensor device depicted in FIG. 9.

In other exemplary implementations, the pinholes may be replaced with diffractive optical elements (e.g., Fresnel zone plates), such that an array of diffractive optical elements are used to act on the light reaching the detector or project an array of sub-images to the detector below. Also, other aperture layers that contain light blocking regions and apertures that act on the light may be included in the display stack and used to capture the fingerprint image through the display using the detector below.

In another exemplary embodiment, two different wavelengths of light from the display pixels are used for pulse detection. This may be used in conjunction with the under display sensor, or in alternative implementations, may be used with other detectors such as detector elements formed in the TFT layers of the display. For example, two sub-pixels of a display stack (e.g., red and green sub-pixels) may be used by an optical sensor under a display for pulse detection. Blue or violet may also be used instead of green. Other wavelengths are possible provided sufficient contrast and the appropriate response to vascular variations.

In general, fingerprint sensors may be susceptible to detecting and authorizing an artificial finger (e.g., a spoof) if it presents the same pattern of ridges and valleys as an authorized finger. Additional security is thus provided by verifying that a biometric input corresponding to a living finger. In this exemplary embodiment, an optical fingerprint sensor is used to measure the vascular flow in the finger by detecting two colors of light (e.g. red and green) reflected from a sensing region, whereby the two colors of light are provided by sub-pixels of the display. By doing so, this exemplary embodiment reduces the risk of spoof or morbid fingers being used to gain unauthorized access. Alternatively, this may be used to repurpose or enhance an optical fingerprint sensor in a display device to provide auxiliary functionality, such as pulse detection for health monitoring.

Pulse oximetry using red and green illumination is described, for example, in C. M. Lochner et al., "All-organic optoelectronic sensor for pulse oximetry," *Nature Communications* 5, Article number: 5745, DOI: 10.1038/ncomms6745 (Dec. 10, 2014), available at <http://www.nature.com/ncomms/2014/141210/ncomms6745/full/ncomms6745.html>. The absorption spectrum on Oxy-hemoglobin (HbO2) and Deoxy-hemoglobin (Hb) differ strongly at about 640 nm (red), and are similar at 540 nm (green). The difference in the absorption of flesh at those two wavelengths is a measure of the oxygenation of the hemoglobin. During each pulse of the heart, arteries bulge with oxygenated blood, then then that blood is deoxygenated before arriving in the veinous return flow. Hence the tissue appears to pulse reddish with each bolus of arterial blood delivered. This visible pulse is detected by comparing the red light returned to the sensor, using the green illumination signal as a reference.

Figure 10:
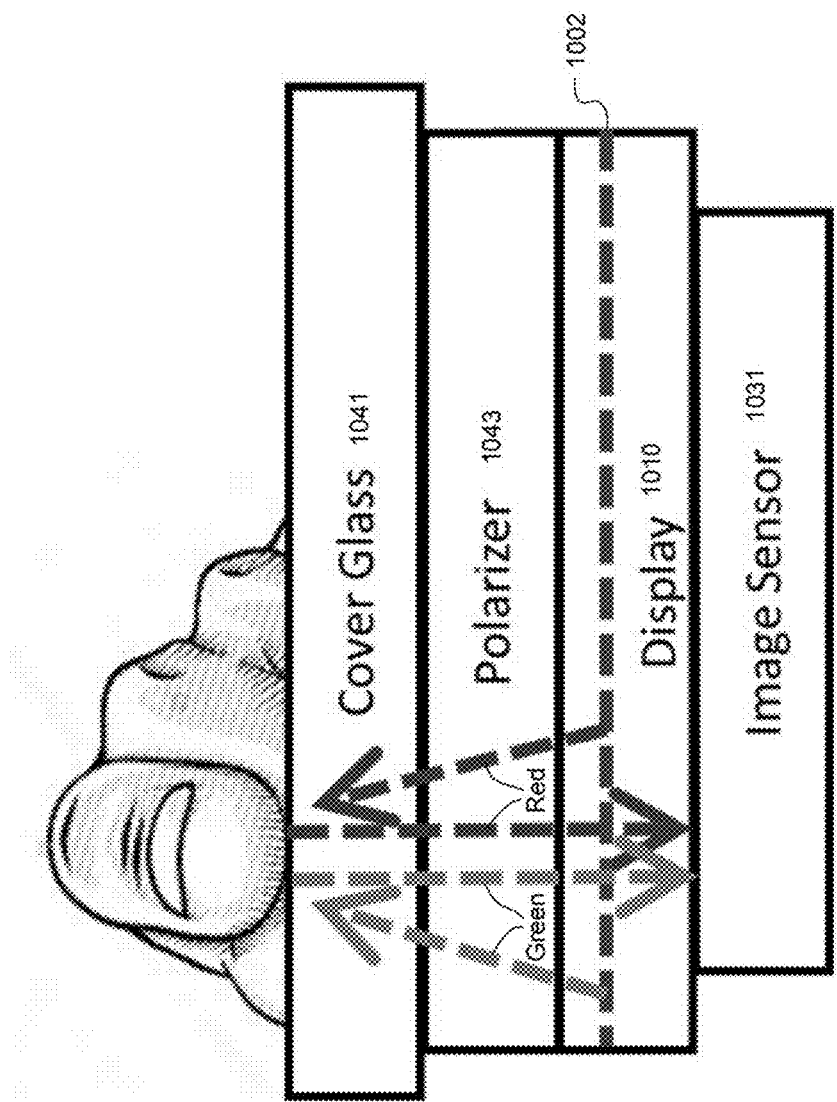
FIG. 10 is a block diagram of an example optical fingerprint sensor sensing red and green light through an aperture layer in a display stack.

The exemplary implementation of FIG. 10 uses the red and green illumination from a display with the light detection being performed by an optical fingerprint sensor under the display. FIG. 10 is a block diagram of an example optical fingerprint sensor sensing red and green light through an aperture layer 1002 in a display stack 1010 (e.g., the aperture layer 1002 is provided beneath the display elements based on apertures corresponding to gaps in TFT/OLED features of the display stack or based on a separate layer with apertures provided below the TFT/OLED features, for example, as discussed above with respect to FIGS. 4 and 7). Red and green light from the display elements of the display stack 1010 (e.g., from red and green sub-pixels) are used to illuminate a finger on an input surface at the top of or above cover glass 1041. The cover glass 1041 is attached to a polarizer (or "polarizer film") 1043, and the polarizer 1043 is attached to the display stack 1010. Below the display stack 1010 is an image sensor 1031 configured to detect light (e.g., red and green light) from the display elements reflected from the sensing region.

In an exemplary implementation, the display 1010 (e.g., an OLED display having green and red sub-pixels) can be controlled via appropriate programming on a processor or processing system to alternately illuminate a biometric object such as a finger with red and green light. The detector receives the alternating red and green light reflected from a sensing region through apertures in an aperture layer of the display stack. Each red frame can be compared to the adjacent green frame to get a relative measure of blood oxygenation, and over the course of one or more heartbeats, that relative signal can be seen to increase and decrease in synchrony with the pulse. The frequency of those increases and decreases is a direct measure of the individual's heart beat rate, and thus the processor can be configured to detect a pulse corresponding to the biometric object (including the detection of whether a pulse is present or absent and/or the detection of a pulse measurement). Further, the magnitude of the red/green variation may also indicate the absolute oxygenation level, or a measure of blood oximetry, allowing the processor further to determine, based on the detection of the red light and the green light reflected from the sensing region, an oxygenation level or measure of blood oximetry corresponding to the biometric object. This measurement method may be referred to as "pulsating photoplethysmogram" or PPG.

In an alternative exemplary implementation, illumination by two wavelengths can be simultaneous if the detector has separate pixels for the two colors. For example, a color filter on the sensors may be used to distinguish the colors. Alternatively, the detector may utilize broadband absorption, while the light source is modulated. A typical mobile device display can change frames at 60 Hz. Thus, for an optical fingerprint sensor in a mobile device application, if alternating frames illuminate red and green subpixels, the sensor can temporally distinguish the red and green signals.

Thus, while conventional solutions require dedicated light sources to provide the different wavelengths of light used for wavelength-dependent reflectivity measurements, in the exemplary implementation of FIG. 10, this is avoided by repurposing the already available multi-spectral light emitting capabilities of the display itself to provide auxiliary functionality to the fingerprint sensor, e.g., pulse detection for anti-spoofing or health monitoring purposes.

Figure 11:
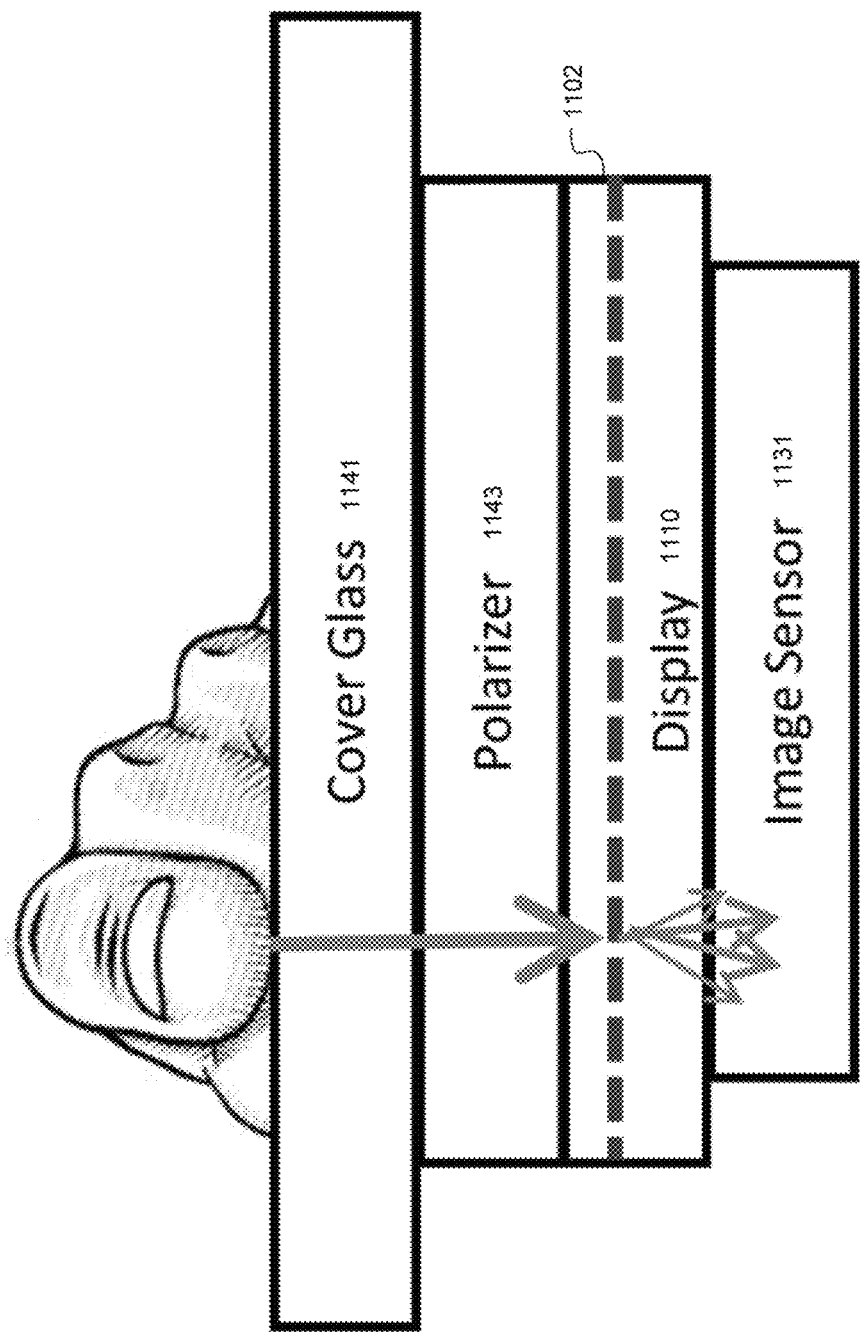
FIG. 11 is a block diagram of an example optical fingerprint sensor device with an aperture layer in a display stack having relatively small apertures configured to diffract light into diffraction patterns.

In another exemplary embodiment, an optical sensor under a display utilizes diffraction imaging to determine features of an input biometric object. As discussed above, display stacks used for mobile device displays include one or more layers of wiring and display elements which may include small gaps or openings which allow light to pass through. In this exemplary embodiment, these small gaps or openings are used as small apertures which provide diffraction of the light passing through into complex patterns. FIG. 11 is a block diagram of an example optical fingerprint sensor device with an aperture layer 1102 in a display stack 1110 having relatively small apertures configured to diffract light into diffraction patterns. It will be appreciated that the type of diffraction patterns generated by the apertures may be based on the shape of the apertures.

As shown in FIG. 11, light reflected from a sensing region for an input biometric object (such as a fingerprint) passes through cover glass 1141, polarizer 1143, and aperture layer 1102 of a display stack 1110, and is detected by an image sensor 1131. A processing system (not depicted) connected to the image sensor 1131 deconvolves the diffraction patterns detected by the image sensor to determine features of the input biometric object and/or generate an image of the input biometric object.

Figure 12:
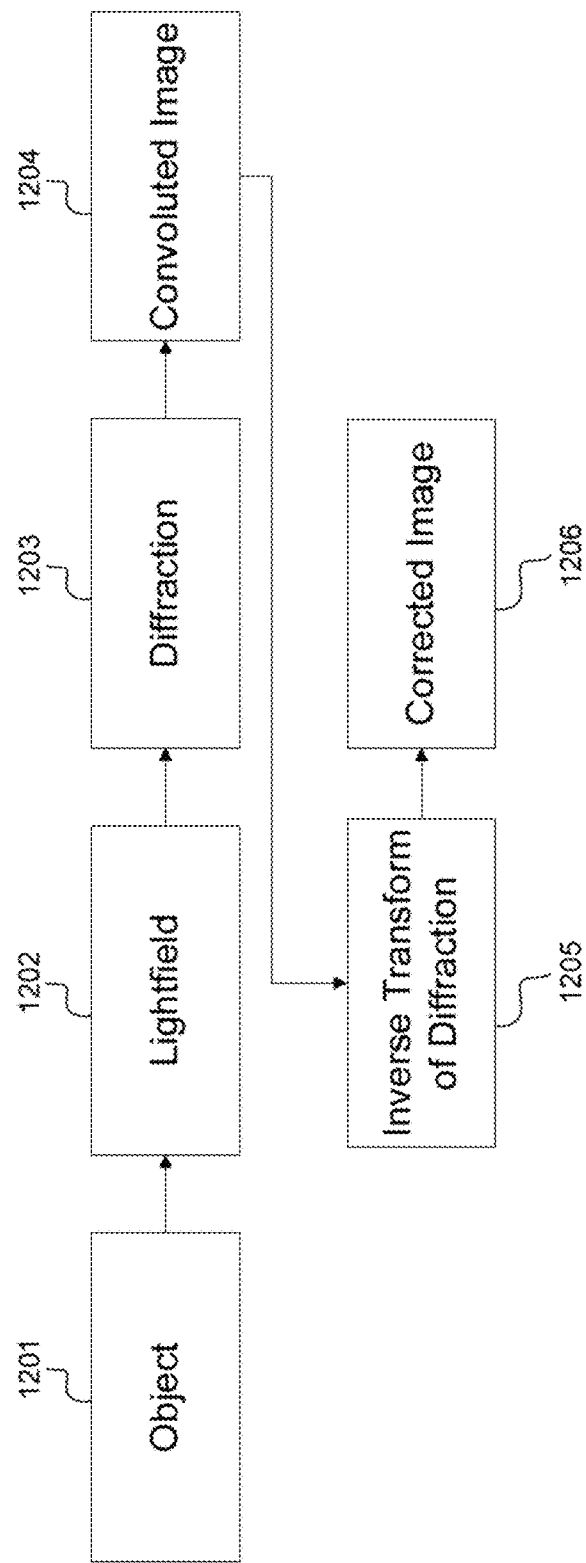
FIG. 12 is a flowchart illustrating an exemplary process for obtaining an image of the input biometric object based on diffraction-based imaging.

FIG. 12 is a flowchart illustrating an exemplary process for obtaining an image of the input biometric object based on the diffraction-based imaging discussed above with respect to FIG. 11. In this exemplary implementation, a lightfield 1202 corresponding to the input biometric object 1201 is diffracted by aperture layer 1102 into diffraction patterns 1203, and a convoluted image 1204 is detected by the image sensor 1131. The processing system then performs an inverse transform of the diffraction 1205 to arrive at a corrected image 1206 corresponding to the input biometric object.

Relative to optical sensor devices relying only on collimators, this exemplary embodiment is able to gather relatively more light at a given resolution. This exemplary embodiment is also relatively simple to manufacture.

In a further exemplary embodiment, diffraction imaging can be used in conjunction with a collimator to limit the portion of the diffraction pattern that is to be received at the image sensor. A shallow or weak collimator can limit the diffraction pattern to a few peaks, reducing the complexity of the inverse transform calculation to a relatively simple deconvolution. A higher aspect ratio collimator can further pick out only the central peak of the diffraction pattern, so that no deconvolution is needed to arrive at the image of the input biometric object. In an exemplary implementation, this collimator may be less restrictive (e.g., it can utilize a lower effective aspect ratio) relative to a collimator that would be needed to provide a clear image without the diffractive element present.

In a further exemplary embodiment, a small point of light at the object plane may be provided as a stimulus and its response can be measured by the optical sensor. This can be used to measure the diffraction pattern at the image plane, and this finite impulse response can be inverted to create the deconvolution transform used for subsequent imaging of the object (e.g., fingerprint).

It will be appreciated that although the examples discussed herein demonstrate the exemplary implementations of the disclosure with respect to fingerprint sensors, these techniques may also be used in other embodiments for other types of sensors having different resolutions beyond just sensors configured to detect fingerprint patterns.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An optical sensor system, comprising:
    an input surface providing a sensing region for a biometric object;
    a plurality of display elements, disposed beneath the input surface, configured to emit light to provide a display, wherein the plurality of display elements are formed on a thin-film transistor (TFT) layer;
    an aperture layer, disposed beneath the plurality of display elements;
    a collimator layer, disposed beneath the aperture layer; and
    a plurality of light sensing elements, disposed beneath the collimator layer, wherein the plurality of light sensing elements are configured to detect light from the sensing region that has passed through the aperture layer and the collimator layer;
    wherein the TFT layer comprises apertures in addition to apertures of the aperture layer.

2. The optical sensor system according to claim 1, wherein the plurality of display elements comprise a plurality of light-emitting diodes (LEDs) or organic light-emitting diodes (OLEDs), wherein the plurality of LEDs or OLEDs are a source for the light from the sensing region.

3. The optical sensor system according to claim 1, wherein the input surface is part of a cover lens; and
    wherein the optical sensor system further comprises a polarizer film between the plurality of display elements and the cover lens.

4. The optical sensor system according to claim 1, wherein the collimator layer further comprises:
    a gap or a transparent layer; and
    a plurality of light-blocking structures forming a collimator beneath the gap or the transparent layer.

5. The optical sensor system according to claim 4, wherein the plurality of light-blocking structures are formed of etched silicon.

6. The optical sensor system according to claim 4, wherein the plurality of light-blocking structures have heights of 100 um or less.

7. The optical sensor system according to claim 4, wherein the plurality of light-blocking structures have vertical walls.

8. The optical sensor system according to claim 4, wherein the plurality of light-blocking structures have slanted walls.

9. The optical sensor system according to claim 1, wherein the aperture layer and the collimator layer are configured to provide an aspect ratio of at least 15:1 for the light passing through the aperture layer and the collimator layer.

10. The optical sensor system according to claim 1, further comprising:
    an auxiliary light source, configured to provide light to the sensing region, wherein the light from the light source is reflected from the sensing region, passed through the aperture layer, and detected by the plurality of light sensing elements.

11. The optical sensor system according to claim 1, wherein the plurality of display elements and the aperture layer are part of a display stack.

12. The optical sensor system according to claim 1, wherein the aperture layer, the collimator layer, and the plurality of light sensing elements are part of an optical biometric sensor attached to a display stack.

13. The optical sensor system according to claim 1, wherein the apertures of the aperture layer are aligned to respective light collimating areas of the collimator layer, wherein the light collimating areas are disposed between light blocking portions of the collimator layer.

14. The optical sensor system according to claim 1, wherein the aperture layer is part of the thin-film transistor (TFT) layer.

15. The optical sensor system according to claim 1, wherein the apertures of the aperture layer are non-circular, and the apertures of the aperture layer are oriented such that sides of nearest adjacent apertures are not facing one another.

16. An optical sensor system, comprising:
    an input surface providing a sensing region for a biometric object;
    a plurality of display elements, disposed beneath the input surface, configured to emit light to provide a display;
    a pinhole layer, comprising a plurality of pinholes, disposed beneath the plurality of display elements; and
    an image sensor, disposed beneath the pinhole layer, wherein the image sensor is configured to detect a plurality of sub-images corresponding to the biometric object, each sub-image of the plurality of sub-images being projected onto a plurality of pixels of the image sensor by a respective pinhole of the pinhole layer.

17. The optical sensor system according to claim 16, further comprising:
    a processing system, configured to combine the detected plurality of sub-images into an image of the biometric object.

18. An optical sensor system, comprising:
    an input surface providing a sensing region for a biometric object;
    a plurality of display elements, disposed beneath the input surface, configured to emit light to provide a display;

an aperture layer, disposed beneath the plurality of display elements, configured to diffract light from the plurality of display elements reflected from the sensing region; and an image sensor, disposed beneath the aperture layer, wherein the image sensor is configured to detect the diffraction patterns of the diffracted light.

19. The optical sensor system according to claim 18, further comprising:
a collimator layer, configured to limit the diffraction patterns of the diffracted light to a central peak for detection by the image sensor.

20. The optical sensor system according to claim 18, further comprising:
a collimator layer, configured to limit each of the diffraction patterns to a central peak and first-order maxima for detection by the image sensor; and
wherein the system further comprises a processor, configured to deconvolve the limited diffraction patterns detected by the image sensor.

21. A method for producing an optical biometric sensor for a display device, comprising:
forming a display stack, wherein the display stack includes an input surface providing a sensing region for a biometric object and a plurality of display elements configured to emit light to provide a display, wherein the plurality of display elements are formed on a thin-film transistor (TFT) layer;
forming a biometric object sensor, wherein the biometric object sensor includes a collimator layer and a plurality of light sensing elements;
forming an aperture layer comprising a plurality of apertures; and
attaching the biometric object sensor to the display stack;
wherein the TFT layer comprises apertures in addition to the apertures of the aperture layer.

22. The method according to claim 21, wherein the aperture layer is formed as part of the display stack.

23. The method according to claim 21, wherein the aperture layer is formed as part of the biometric object sensor.

24. An optical sensor system, comprising:
an input surface providing a sensing region for a biometric object;
a plurality of display elements, disposed beneath the input surface, configured to emit light to provide a display, wherein the plurality of display elements are formed on a thin-film transistor (TFT) layer;
an aperture layer, wherein the aperture layer is part of the thin-film transistor (TFT) layer and is disposed beneath the plurality of display elements;
a collimator layer, disposed beneath the aperture layer; and
a plurality of light sensing elements, disposed beneath the collimator layer, wherein the plurality of light sensing elements are configured to detect light from the sensing region that has passed through the aperture layer and the collimator layer.

25. An optical sensor system, comprising:
an input surface providing a sensing region for a biometric object;
a plurality of display elements, disposed beneath the input surface, configured to emit light to provide a display;
an aperture layer, disposed beneath the plurality of display elements, wherein apertures of the aperture layer are non-circular, and the apertures are oriented such that sides of nearest adjacent apertures are not facing one another;
a collimator layer, disposed beneath the aperture layer; and
a plurality of light sensing elements, disposed beneath the collimator layer, wherein the plurality of light sensing elements are configured to detect light from the sensing region that has passed through the aperture layer and the collimator layer.

26. An optical sensor system, comprising:
an input surface providing a sensing region for a biometric object, wherein the input surface is part of a cover lens;
a plurality of display elements, disposed beneath the input surface, configured to emit light to provide a display;
an aperture layer, disposed beneath the plurality of display elements;
a collimator layer, disposed beneath the aperture layer;
a plurality of light sensing elements, disposed beneath the collimator layer, wherein the plurality of light sensing elements are configured to detect light from the sensing region that has passed through the aperture layer and the collimator layer; and
a polarizer film between the plurality of display elements and the cover lens.

27. An optical sensor system, comprising:
an input surface providing a sensing region for a biometric object;
a plurality of display elements, disposed beneath the input surface, configured to emit light to provide a display;
an aperture layer, disposed beneath the plurality of display elements;
a collimator layer, disposed beneath the aperture layer; and
a plurality of light sensing elements, disposed beneath the collimator layer, wherein the plurality of light sensing elements are configured to detect light from the sensing region that has passed through the aperture layer and the collimator layer;
wherein the collimator layer further comprises:
a gap or a transparent layer; and
a plurality of light-blocking structures forming a collimator beneath the gap or the transparent layer, wherein the plurality of light-blocking structures have heights of 100 um or less.

* * * * *